United States Patent
Czipott et al.

(10) Patent No.: US 6,956,369 B2
(45) Date of Patent: Oct. 18, 2005

(54) SCREENING METHOD AND APPARATUS (75) Inventors: Peter V. Czipott, San Diego, CA (US); Sankaran Kumar, San Marcos, CA (US); Stephen Wolff, San Diego, CA (US); Lowell J. Burnett, El Cajon, CA (US)

(73) Assignees: MedNovus, Inc., Leucadia, CA (US); Quantum Magnetics, Inc., San Diego, CA (US)

( * ) Notice: Subject to any disclaimer, the term of this patent is extended or adjusted under 35 U.S.C. 154(b) by 0 days.

(21) Appl. No.: 10/723,457

(22) Filed: Nov. 25, 2003

(65) Prior Publication Data

US 2004/0169509 A1 Sep. 2, 2004

Related U.S. Application Data (63) Continuation-in-part of application No. 10/703,147, filed on Nov. 5, 2003, which is a continuation of application No. 10/681,033, filed on Oct. 7, 2003, said application No. 10/723,457, is a continuation-in-part of application No. 10/681,033.
(60) Provisional application No. 60/440,697, filed on Jan. 17, 2003, and provisional application No. 60/489,250, filed on Jul. 22, 2003.

(51) Int. Cl.$^7$ .............................................. G01R 33/00
(52) U.S. Cl. ........................ 324/244; 324/228; 324/260
(58) Field of Search ............................. 324/200–201, 324/228, 214, 234, 239, 242–246, 248–249, 257–262; 600/407, 409–410, 420–421

(56) References Cited

U.S. PATENT DOCUMENTS

| 6,133,829 A | 10/2000 | Johnstone et al. |
| 2004/0135687 A1 | 7/2004 | Keene |

FOREIGN PATENT DOCUMENTS

| WO | WO 03091753 | 11/2003 |
| WO | WO 03/091753 A1 | 11/2003 |
| WO | WO 04/044620 A1 | 5/2004 |

OTHER PUBLICATIONS

ETS–LINDGREN; *Ferroguard Unveiled at RSNA 2003*; The Quiet Zone; Jan., 2004; p. 11.
ETS–LINDGREN Website; *Ferromagnetic Detection System*; May 29, 2004; 2 pages.

(Continued)

*Primary Examiner*—Bot LeDynh
(74) *Attorney, Agent, or Firm*—Gerald W. Spinks (57) ABSTRACT

A method and apparatus to screen individuals specifically for paramagnetic or ferromagnetic objects they may be carrying or wearing, before they enter a controlled area. The device comprises a screening portal, including at least one magnetic gradiometer and its electronics. The device places all of the sensor arrays in close proximity to a subject's body, for screening purposes. The portal has at least one excitation coil oriented to cause the excitation field to have zero mutual inductance with the gradiometers.

19 Claims, 6 Drawing Sheets

OTHER PUBLICATIONS

CMP United Business Media Website; Metal detector guards the door to screen ferromagnetic objects; Diagnostic Imaging SCAN; Jan. 28, 2004; 2 pages.

Finn, Edward J., et al., Ferromagnetic Materials in Patients: Detection before MR Imaging; Radiology; Jul. 1985; vol. 185; pp. 139–141.

Institute for Biodiagnostics; MRI Safety: Detection of Ferromagnetic Objects; Date unknown; 8 pages; National Research Council Canada.

Kopp Development; Ferralert Brochure; Date Unknown; 2 pages; Kopp Development; Jensen Beach, FL.

Kotter, David K., et al..; Abstract: Detection and Classification of Concealed Weapons Using a Magnetometer–based Portal; NASA ADS Instrumentation Abstract Service; Aug., 2002; 1 page; The International Society for Optical Engineering.

Melodi Metal Locator Gets Straight to the Point; Medica 2002; Nov., 2002; 4 pages; Düsseldorf, Germany.

Metal Detector Finds Lost Coins in Kids; CNN.com/TECHNOLOGY; Jan. 29, 2003;2 pages; Cable News Network.

Quantum Magnetics; i–Portal 100 Advanced Weapons Detection Portal Brochures; Date unknown; 8 pages.

Mednovus/Quantum Magnetics; Safescan Portal 9000 Series Brochure; 1 page.

SCREENING METHOD AND APPARATUS

CROSS REFERENCE TO RELATED APPLICATIONS

This is a continuation-in-part application of co-pending U.S. application Ser. No. 10/681,033, filed Oct. 7, 2003, for "Magnetic Resonance Imaging Screening Method and Apparatus". This is also a continuation-in-part application of co-pending U.S. application Ser. No. 10/703,147, filed Nov. 5, 2003, for "Security Screening Method and Apparatus", which is a continuation application of co-pending U.S. application Ser. No. 10/681,033, filed Oct. 7, 2003, for "Magnetic Resonance Imaging Screening Method and Apparatus". This application relies upon U.S. Provisional Pat. App. No. 60/440,697, filed Jan. 17, 2003, for "Method and Apparatus to Use Magnetic Entryway Detectors for Pre-MRI Screening".

STATEMENT REGARDING FEDERALLY SPONSORED RESEARCH OR DEVELOPMENT

Not Applicable

BACKGROUND OF THE INVENTION

1. Field of the Invention

The present invention is in the field of methods and apparatus used to prevent the presence of paramagnetic or ferromagnetic objects in a controlled area.

2. Background Art

It can be desirable to exclude paramagnetic and ferromagnetic objects from a controlled area. For instance, paramagnetic and ferromagnetic objects are highly unsafe near MRI systems, because the strong magnetic gradients caused by MRI magnets exert a strong force on such objects, potentially turning them into dangerous missiles. Several accidents, some fatal, are known to have occurred as the result of someone inadvertently carrying such an object into the MRI room. Current MRI safety practices rely on signage and training to prevent people from taking such objects into the MRI chamber. Paramagnetic and ferromagnetic objects which can be weapons may also be unsafe in other controlled areas, such as schools.

Use of known conventional metal detectors, whether portals or wands, would not be efficient for this purpose. Conventional systems generate an audio-band oscillating or pulsed magnetic field with which they illuminate the subject. The time-varying field induces electrical eddy currents in metallic objects. It is these eddy currents which are detected by the system, to reveal the presence of the metallic objects.

BRIEF SUMMARY OF THE INVENTION

The present invention provides an apparatus and a method for scanning a subject for the presence of an object which is either permanently magnetic or susceptible to being magnetized by an external field. The sensors in this scanning apparatus can be mounted on a portal type frame. This positions the entire sensor array in proximity to a subject. The portal arrangement of the scanner arranges the sensors suitably for positioning every sensor in proximity to the body of a subject, as the subject passes through the portal.

The sensors can detect the magnetic field of the object, whether the object is a permanent magnet or merely susceptible to magnetization. Where an external field induces a magnetic field in the object, the external field may be the Earth's magnetic field, or it may be generated by another source, such as a nearby MRI apparatus or a dedicated source such as one mounted on the frame of the apparatus.

The novel features of this invention, as well as the invention itself, will be best understood from the attached drawings, taken along with the following description, in which similar reference characters refer to similar parts, and in which:

DETAILED DESCRIPTION OF THE INVENTION

The present invention, which applies to both permanently magnetic objects called "hard" ferromagnets and non-permanent magnetically susceptible objects called "soft" ferromagnets, can use magnetometers with good sensitivity at frequencies all the way, or nearly, to DC, i.e., zero frequency. This allows several modes of use:

(1) As a completely passive system, the present invention detects ferromagnetic objects using their permanent magnetization, in the case of "hard" ferromagnets, or the magnetization induced by the Earth's magnetic field, in the case of "soft" ferromagnets.

(2) As a DC magnetic susceptometer, the present invention applies a static DC magnetic field, allowing control and usually enhancement of the magnetization of soft ferromagnets, thus enhancing their detectability.

(3) As an AC magnetic susceptometer, the present invention applies an oscillating AC magnetic field, but at very low frequencies compared to conventional detectors, allowing enhancement of their magnetization. The purpose of AC illumination is to move the signal from DC to a region of lower noise at finite frequency. The AC frequency is preferably chosen to avoid inducing the electrical eddy currents detected by other systems, to suppress the response from non-ferromagnetic metal objects, and thus maintaining the discrimination capability.

The present invention importantly arranges an array of sensors in such a way that the entire sensor array can be placed in proximity to the body of a subject, such as a patient or an attendant. Further, the sensor arrays can be arranged so as to be susceptible to placement in proximity to the body of a subject, such as a patient lying recumbent, as on a stretcher or gurney.

A passive magnetic embodiment of the portal used in one embodiment of the present invention can be similar in some respects to the SecureScan 2000™ weapons detection portal which is manufactured by Quantum Magnetics, Inc., and marketed by Milestone Technology, Inc., or the i-Portal™ weapons detection portal which is marketed by Quantum Magnetics, Inc.

The portal includes two panels of sensors on the sides of the entryway. An array of magnetometers inside each panel enables detection, characterization, and localization of ferromagnetic objects from the soles of the feet to the top of the head. The magnetometer array can take a variety of configurations, and it can use a variety of sensor technologies. For example, a set of 16 single-axis magnetic gradiometers can be arranged with 8 in each panel. Other configurations can include arrays of multi-axis gradiometers, or combinations of single-axis and multi-axis gradiometers. One or more magnetic tensor gradiometers may also be used. A magnetoresistive magnetometer, or any other sensor capable of sensing magnetic field changes at or near zero frequency, can be used.

Figure 1:
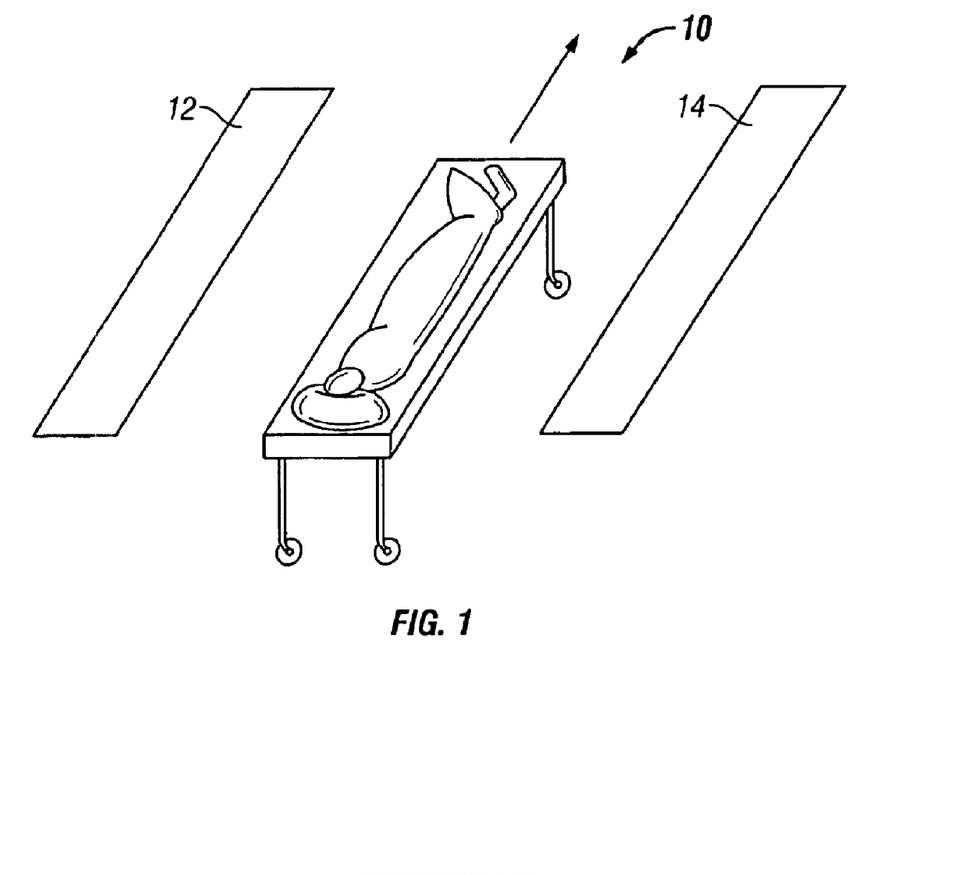
FIG. 1 is a schematic showing the horizontal arrangement of sensor arrays in a first portal type embodiment.

As shown in FIG. 1, in order to scan a patient on a gurney, the portal sensor configuration 10 of the present invention can be arranged to bring all of the sensors closer to the patient and to effectively scan a patient in the recumbent position. Rather than being arranged vertically, the two sensor panels 12, 14 can be arranged horizontally, parallel to the path of the gurney and on either side, as shown in FIG. 1. This places the sensors in a similar relation to the patient as they would have, in the vertical arrangement, to an ambulatory patient. Also, a single "snapshot" of data covers the entire gurney and patient, as in the ambulatory case. The sensor panels 12, 14 can be permanently arranged horizontally, or they can pivot to this configuration.

Figure 2:
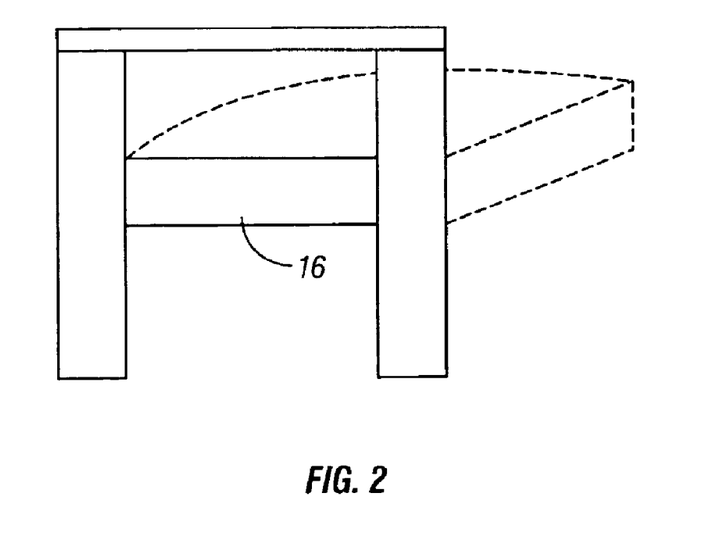
FIG. 2 is a schematic of a second portal embodiment.
Figure 3:
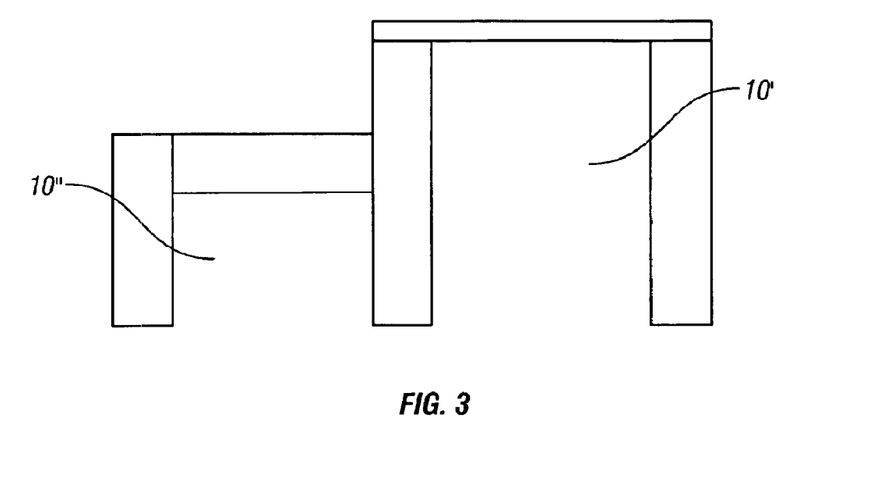
FIG. 3 is a schematic of a third portal embodiment.

Alternatively, in addition to the vertically arranged sensor panels as in the aforementioned known portals, the portal can have a "dutch door" with an additional, horizontal, sensor panel 16 in the upper half of the door, just high enough to clear a patient on a gurney, as shown in FIG. 2. As the patient is wheeled under the upper door, the patient would pass in close proximity to the horizontal sensor panel 16, allowing all of its sensors to scan the patient from head to foot, or vice versa. This gives the best detection and resolution of objects, since more sensors are placed closer to the patient. Then, the attendant would push the dutch door open and walk through the portal, being scanned by the vertically arranged sensor panels. The "dutch door" array 16 can be spring loaded, so that it moves out of the way for an ambulatory subject. A microswitch indicator can tell the software whether the door is engaged, for a recumbent patient, or disengaged, for an ambulatory subject. As a variation of this embodiment, a portal with vertically arranged sensor panels can be situated next to a portal with a horizontally arranged sensor panel, as shown in FIG. 3.

As an alternative to the passive magnetic portal, an AC or DC magnetizing field can be provided by one or more source coils, a DC field can be provided by a permanent magnet array, or a DC field can be provided in the form of the fringing field of a nearby MRI magnet. In any case, a computer is provided to interrogate the sensors and to interpret the magnetic signals, to detect, characterize, and locate ferromagnetic objects. Characterization of the object provides the size and orientation of its magnetic moment, which can be related to the physical size of the object, and to the magnitude of the attractive magnetic force. The analysis software can use various known algorithms, or a neural network can be used. The information gained can be related to a photographic image of the subject, for the purpose of locating the ferromagnetic object on the subject. A light display can be used to indicate the approximate location of the detected object. System diagnosis, monitoring, and signal interpretation can be done via the Internet, if desired.

The use of AC fields enables the use of induction coil sensors, in addition to or instead of magnetometers, like magnetoresistive, fluxgate, and other types. Induction coil sensors are impossible to use in the DC embodiment because the induction coil has zero sensitivity at zero frequency. Using induction coil sensors typically reduces the cost of the product without sacrificing sensitivity in the AC system.

An AC system could make use of two different excitation directions—operating at two different frequencies, to avoid crosstalk—which can improve detection of long, narrow objects, which are precisely the shape that is most dangerous in this situation.

The excitation frequency is chosen to be low enough so that the magnetization (or, equivalently, magnetic susceptibility) response of objects to be detected exceeds their eddy current response. The choice of frequency is expected to be less than 1 kHz, but it can be as high as 3 kHz in some applications.

The excitation current can be driven by any number of standard drive circuits, including either direct drive (controlled voltage source in series with the coil) or a resonant drive (voltage source coupled to the coil via a series capacitance whose value is chosen such that, in combination with the coil's self-inductance, the current is a maximum at a desired resonant frequency given by $\frac{1}{2\pi}(LC)^{1/2}$).

The receiver or sensor coil can be made of two coils, wound in opposite senses and connected in series. They form what is well-known as a gradiometer; a uniform magnetic flux threading both coils produces zero response. The coils are distributed symmetrically relative to the excitation coil such that, in the absence of any target object (which is conductive, magnetic or magnetically permeable) nearby, each senses an identical flux from the excitation which thus cancels out.

Although the intent is to make the two coils perfectly identical, and to place them in identically symmetric locations, in practice one falls short of the ideal. As a result, any actual embodiment will display a nonzero response to the excitation, even in the absence of a target; this residual common-mode signal is referred to as an "imbalance" signal. Standard electrical circuits can zero out the imbalance signal by adding an appropriately scaled fraction of the reference voltage $V_{ref}$ (a voltage proportional to the excitation current, obtained by measuring across a series monitor resistor) to the output voltage $V_{out}$.

When a target object is near to either coil, it spoils the symmetry and thus induces a finite signal. This signal oscillates at the same frequency as the excitation. Standard demodulation or phase-sensitive detection circuits, using $V_{ref}$ as the phase reference, measure the magnitude of $V_{out}$ in phase with $V_{ref}$ and in quadrature (90 degrees out of phase) with $V_{ref}$. At an appropriately chosen low frequency, the response will be dominated by the susceptibility response, which appears predominantly in the quadrature output, as opposed to the eddy current response, which appears predominantly in the in-phase component.

In principle, the coils could be replaced by two magnetometer sensors (fluxgate, magnetoresistive, magnetoimpedance, etc.). Coils respond to the time derivative of the magnetic field, while magnetometers respond to the field itself; the coil's output voltage is shifted by 90 degrees with respect to a magnetometer's. If magnetometers are used instead of coils, then the susceptibility response would show up in the in-phase component and the eddy current response (at low frequency) in the quadrature component.

If the operating frequency is chosen much too high, both susceptibility and eddy-current responses appear in the in-phase component (using magnetometers) or quadrature component (using coils), but with opposite sign, making it impossible to distinguish between the two. At intermediate frequencies, the eddy current phase is intermediate between the two components, complicating the distinction. Therefore, it is important to choose the excitation frequency to be low enough, and preferably less than about 3000 Hz.

The substrate or coil form must be nonconductive, non-ferromagnetic and, with one possible exception, magnetically impermeable ($\mu=\mu_o$, where $\mu_o$ is the permeability of free space). The exception is that a magnetically permeable core inside sensor coils having a cylindrical geometry can increase the sensitivity of the system.

The use of a reference sensor helps to eliminate common mode error signals. For instance, a nearby passenger conveyer, such as a gurney, could contain magnetic components, but this spurious magnetization is not what is intended to detect, and, therefore, it is preferable to eliminate this magnetic source.

An audio alert, such as a buzzer, and/or an alarm light can be employed to signal the presence of an unwanted ferromagnetic object.

Figure 4:
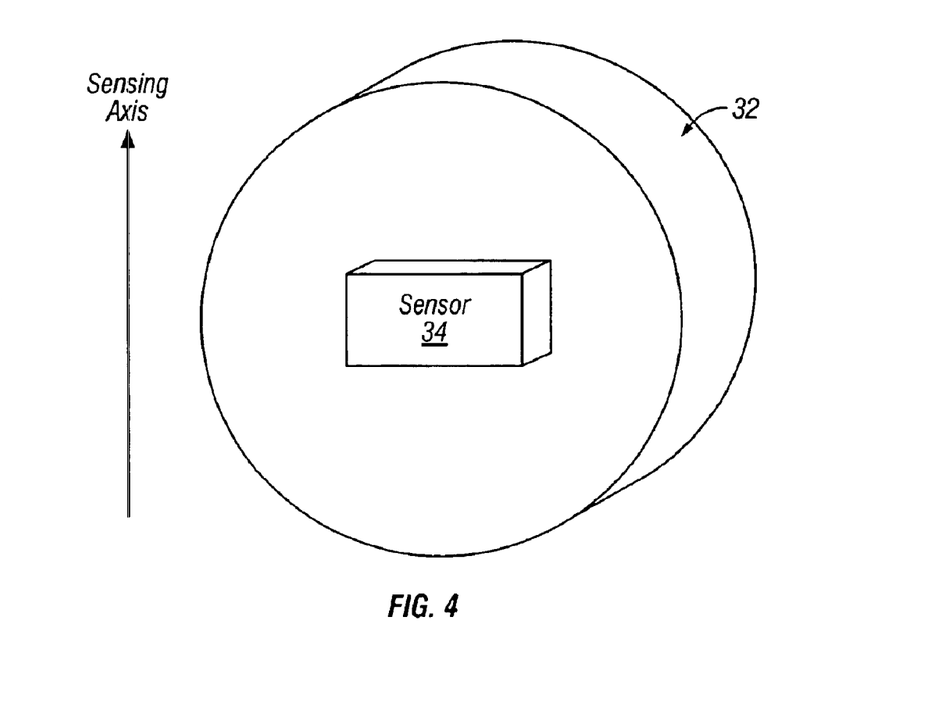
FIG. 4 is a schematic of the arrangement of a permanent magnet source relative to the sensing axis of the sensor.

As shown in FIG. 4, the sensor's sensitivity axis is orthogonal to the axis of the magnetic field of a permanent magnet 32. Otherwise stated, the magnetic field of the permanent magnet 32 is normal to the plane of the sensor 34.

Figure 5:
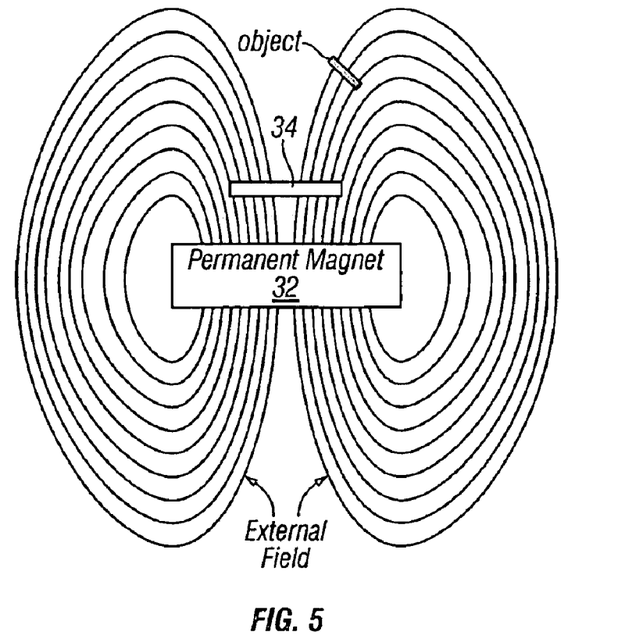
FIG. 5 is a schematic showing the arrangement of the source field from a permanent magnet, a sensor, and a ferromagnetic object.
Figure 6:
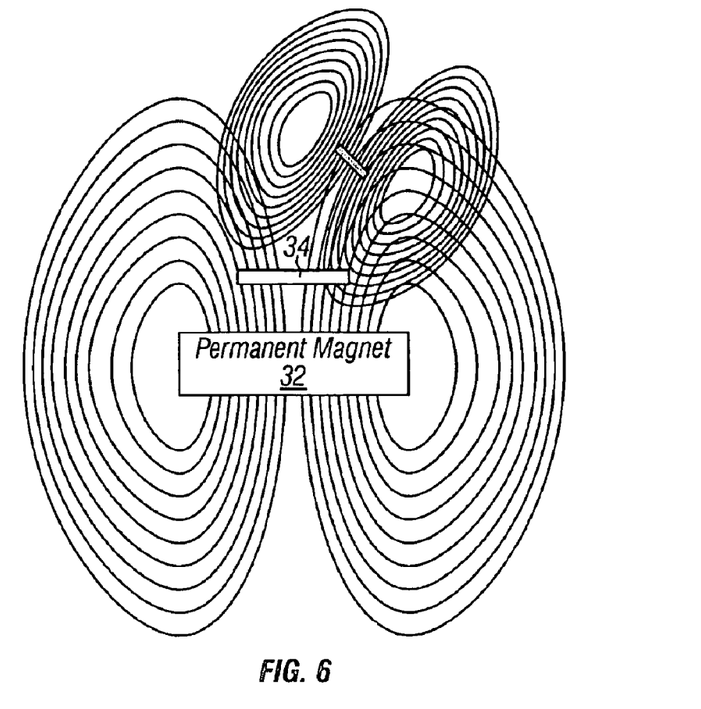
FIG. 6 is a schematic showing the magnetic field of the ferromagnetic object shown in FIG. 5.

In FIG. 5, the magnetic field of the DC permanent magnet field source 32 magnetizes the ferromagnetic object, which then has a magnetic field of its own, as shown in FIG. 6. This induced magnetization ("demag field") is detected by the sensor 34, triggering the alarm buzzer and/or light.

Figure 7:
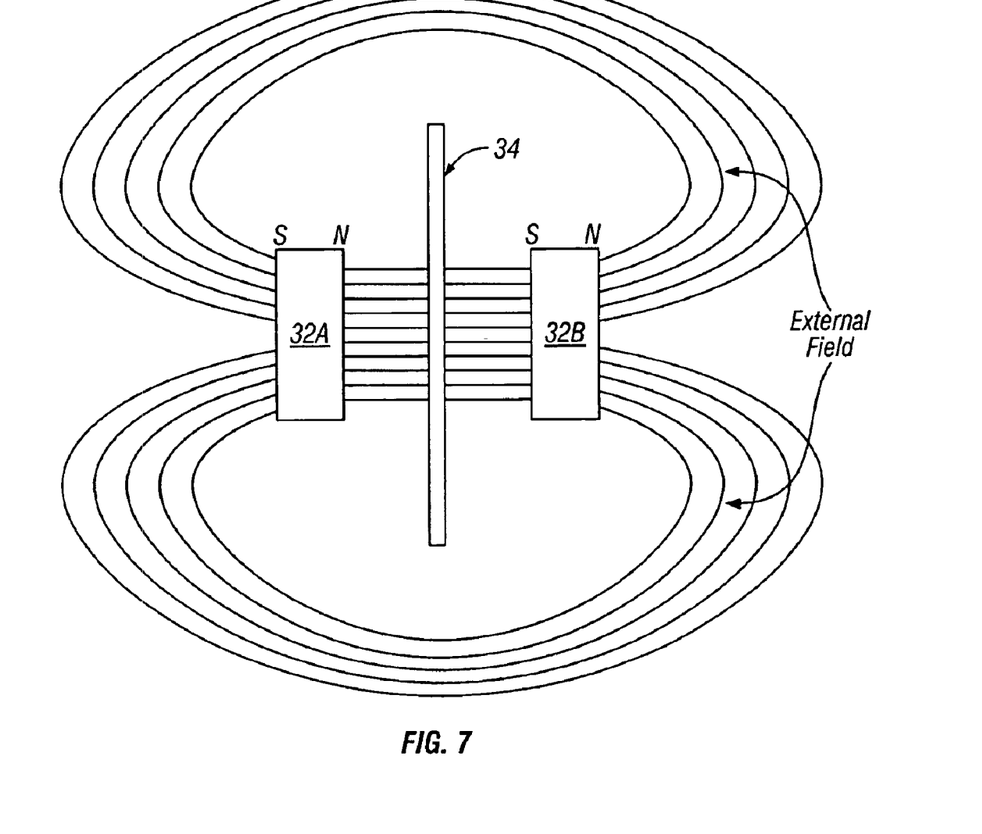
FIG. 7 is a schematic showing the arrangement of a sensor and the source field from two permanent magnets.

An alternative configuration, shown in FIG. 7, utilizes two permanent magnets 32A, 32B, as the magnetic field between them is less divergent than with a single permanent magnet. With the use of two permanent magnets 32A, 32B and less resultant divergence, there is less need for criticality about positioning the permanent magnet with respect to the sensor 34.

FIGS. 8 through 13 show various embodiments of the excitation coil configurations useful with the portal structure, for applying a magnetizing field to the volume of space around a portal, in accordance with the present invention. For the sake of illustration, the portal is assumed to comprise a set of single-axis magnetic field gradiometers in two substantially equal arrays on either side of the opening. The principles can be generalized to portals with gradiometers in other orientations, and with multi-axis gradiometers as well.

The underlying requirement of the applied field is that it should not disturb the sensors. That is, in the absence of a magnetic or magnetizable object in the portal, the field should produce zero signal on the gradiometer outputs. This requirement ensures that variations in the applied field don't show up as noise on the sensors—since the objective is to increase the signal from objects, by increasing the magnetizing field, without increasing the sensor noise.

The requirement can be stated as follows: the magnetizing field should have zero mutual inductance with the sensors. This can be expressed in two forms, with the same net result but with slightly different implementation issues. In one form, the magnetizing field has zero mutual inductance with each magnetometer (a pair of them making one gradiometer). This is a more restrictive requirement than the second form, which specifies zero mutual inductance with each gradiometer.

Assume a coordinate system in which the z-axis points vertically, the x-axis horizontally in the plane of the portal, and the y-axis orthogonally to the plane of the portal. FIGS. 8 through 13 all assume gradiometers measuring the difference in the x-direction of the x-component of the field (written as $\partial B_x/\partial x$). FIGS. 8 through 11 illustrate the first form of the requirement (zero coupling to each magnetometer); this is achieved by making the field point entirely in the y-direction (orthogonally to the sensitive axis) at all the sensors.

Figure 8:
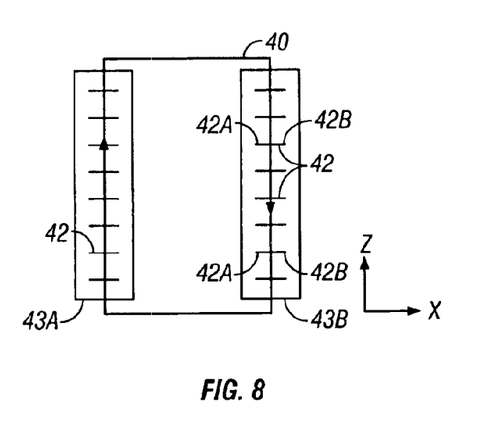
FIGS. 8 and 9 show a first embodiment of the excitation coil configuration relative to the portal structure.
Figure 9:
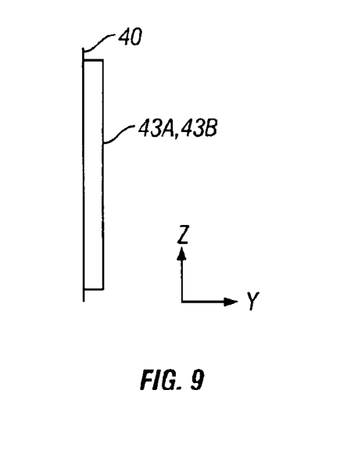

FIGS. 8 and 9 illustrate a single coil in the portal plane, with FIG. 8 showing the front elevation of the portal, and FIG. 9 showing the right side elevation. Not only is the illustrated coil 40 in the plane of the portal, or as close as possible to it, but the vertical legs run midway between each pair of magnetometers 42A, 42B making up the gradiometer pair 42. Thus, not only is the field perpendicular to the magnetometers' sensitive axis, but each sensor of the pair sees the same field, so any residual field gets canceled on subtraction of one sensor signal from the other, to form the gradient measurement. The coil 40 need not be higher or lower than the portal panels 43A, 43B; the components are just shown this way for clarity.

Figures 10, 11:
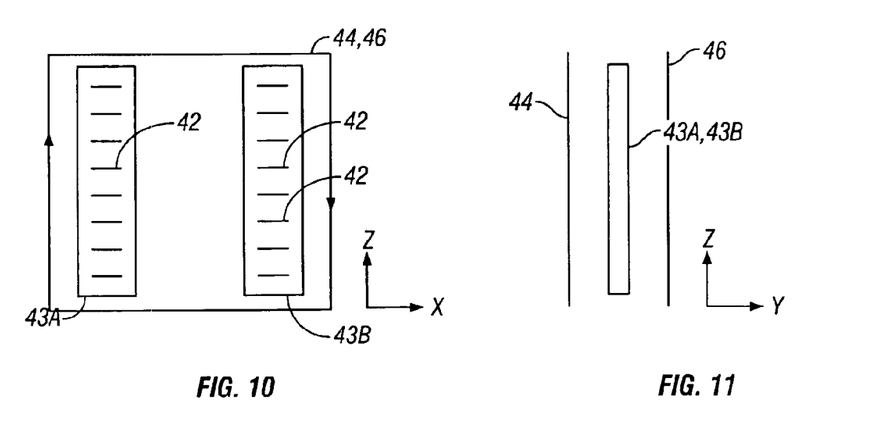
FIGS. 10 and 11 show a second embodiment of the excitation coil configuration relative to the portal structure.

FIGS. 10 and 11 show a pair of coils 44, 46 on either side of the portal plane, with FIG. 10 showing the front elevation of the portal, and FIG. 11 showing the right side elevation. This optimum arrangement is as a Helmholtz coil pair, but this is not mandatory. The Helmholtz configuration gives the best field uniformity over the portal aperture, but it can add some bulkiness to the apparatus, which can create a problem in some applications, such as an especially "space-challenged" MRI facility. The two coils 44, 46 overlap. Current runs in the same direction, clockwise in FIG. 10, in both coils.

Figure 12:
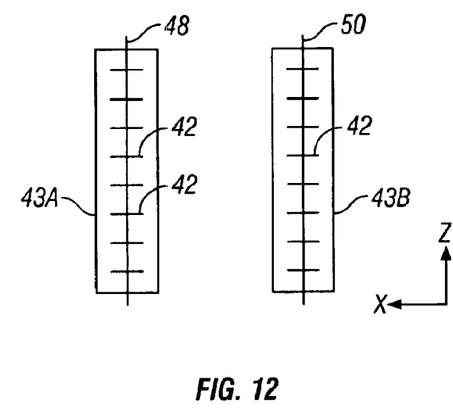
FIGS. 12 and 13 show a third embodiment of the excitation coil configuration relative to the portal structure.
Figure 13:
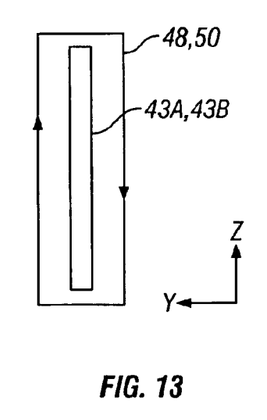

FIGS. 12 and 13 illustrate the second form of the requirement (zero mutual inductance with each gradiometer). In this embodiment, each of two coils 48, 50 creates a field in the x-direction. FIG. 12 shows the front elevation of the portal, and FIG. 13 shows the right side elevation. Positioning is chosen to make the magnetizing field the same at both magnetometers 42A, 42B in each gradiometer 42. Each magnetometer 42A, 42B is located at one end of one of the thin lines denoting the gradiometers 42. By making the excitation field substantially identical for each magnetometer 42A, 42B, the differential (gradient) measurement substantially cancels out the excitation field. The two coils 48, 50 overlap in the view shown in FIG. 13, and they carry current in the same direction, clockwise in the drawing.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. An apparatus for excluding objects from introduction into a controlled area, comprising:
    a portal structure adapted to scan a human subject;
    an array of magnetic field gradiometers mounted on said portal structure, each said gradiometer including a pair of magnetometers adapted to sense an induced magnetic field of an object in at least one sensitive axis, each of said magnetometers being oriented to have its said at least one sensitive axis parallel to said at least one sensitive axis of said other magnetometer of said pair;
    at least one excitation source establishing at least one magnetic excitation field adapted to induce said magnetic field of said object, said at least one excitation source being oriented to cause said at least one excitation field to have a substantially zero mutual inductance with said gradiometer array; and
    a processor adapted to interpret signals from said gradiometer array to indicate the presence of said object.

2. The apparatus recited in claim 1, wherein said at least one excitation source is oriented to cause said at least one excitation field to have a substantially zero mutual inductance with said at least one sensitive axis of each of said magnetometers.

3. The apparatus recited in claim 2, wherein said at least one excitation source is oriented to cause said at least one excitation field to have its axis orthogonal to said at least one sensitive axis of said magnetometers.

4. The apparatus recited in claim 3, wherein said at least one excitation source comprises a single excitation coil, said single excitation coil being substantially co-planar with said gradiometer array.

5. The apparatus recited in claim 4, wherein:
    said gradiometer array comprises first and second gradiometer sub-arrays, said sub-arrays being located on opposite sides of said portal structure;
    said single excitation coil has first and second vertical legs;
    said first vertical leg of said excitation coil bisects each said gradiometer of said first sub-array, substantially equidistant from each said magnetometer of each said gradiometer of said first sub-array; and
    said second vertical leg of said excitation coil bisects each said gradiometer of said second sub-array, substantially equidistant from each said magnetometer of each said gradiometer of said second sub-array.

6. The apparatus recited in claim 3, wherein said at least one excitation source comprises two excitation coils, each said excitation coil being in a plane parallel to the plane of said gradiometer array, said excitation coils being on opposite sides of, and substantially equidistant from, said plane of said gradiometer array.

7. The apparatus recited in claim 6, wherein said two excitation coils comprise a Helmholtz coil arrangement.

8. The apparatus recited in claim 1, wherein said at least one excitation source is oriented to cause said at least one excitation field to have substantially zero mutual inductance with each of said gradiometers.

9. The apparatus recited in claim 8, wherein said at least one excitation source is oriented to cause said at least one excitation field to have its axis parallel to said at least one sensitive axis of said magnetometers.

10. The apparatus recited in claim 9, wherein said at least one excitation source is in a plane bisecting each said gradiometer, substantially equidistant from each said magnetometer of each said gradiometer.

11. The apparatus recited in claim 10, wherein:
    said gradiometer array comprises first and second gradiometer sub-arrays, said sub-arrays being located on opposite sides of said portal structure;
    said at least one excitation source comprises first and second excitation coils;
    said first excitation coil being in a first plane bisecting each said gradiometer of said first sub-array, substantially equidistant from each said magnetometer of each said gradiometer of said first sub-array; and
    said second excitation coil being in a second plane bisecting each said gradiometer of said second sub-array, substantially equidistant from each said magnetometer of each said gradiometer of said second sub-array.

12. A method for excluding objects from introduction into a controlled area, comprising;
    providing an array of magnetic field gradiometers mounted on a portal structure, each said gradiometer including a pair of magnetometers, each said magnetometer being oriented to have its at least one sensitive axis parallel to the at least one sensitive axis of said other magnetometer of said pair;
    providing at least one excitation source;
    establishing at least one magnetic excitation field with said at least one excitation source, while orienting said excitation source to cause said at least one excitation field to have zero mutual inductance with said gradiometer array;
    scanning a subject with said gradiometer array;
    inducing a magnetic field in an object, with said at least one excitation field;
    sensing said induced magnetic field of said object, with said gradiometer array; and
    interpreting signals from said gradiometer array, with a processor, to indicate the presence of said object.

13. The method recited in claim 12, wherein said at least one excitation source comprises an excitation coil, and further comprising energizing said excitation coil with alternating current.

14. The method recited in claim 13, further comprising establishing said alternating current with a frequency of less than approximately 3000 Hz.

15. The method recited in claim 12, further comprising orienting said at least one excitation source to cause said at least one excitation field to have zero mutual inductance with said at least one sensitive axis of each of said magnetometers.

16. The method recited in claim 15, further comprising orienting said at least one excitation source to cause said at least one excitation field to have its axis orthogonal to said at least one sensitive axis of said magnetometers.

17. The method recited in claim 16, wherein said at least one excitation source comprises two excitation coils, further comprising:
    locating said excitation coils in planes parallel to, on opposite sides of, and substantially equidistant from, the plane of said gradiometer array;
    energizing said two excitation coils to establish a substantially non-diverging excitation field across said portal structure.

18. The method recited in claim 12, further comprising orienting said at least one excitation source to cause said at least one excitation field to have zero mutual inductance with each of said gradiometers.

19. The apparatus recited in claim 18, further comprising orienting said at least one excitation source to cause said at least one excitation field to have its axis parallel to said at least one sensitive axis of said magnetometers.

* * * * *